United States Patent

Macchiarulo et al.

[11] Patent Number: 5,307,672
[45] Date of Patent: May 3, 1994

[54] METHOD AND APPARATUS TO CHECK THE STATE OF WEAR IN A COVERING FABRIC OF A DRIVING BELT

[75] Inventors: Vincenzo Macchiarulo, Pescara; Giovanni Foia, Vasto, both of Italy

[73] Assignee: Pirelli Transmissioni Industriali S.p.A., Chieti, Italy

[21] Appl. No.: 922,516

[22] Filed: Jul. 31, 1992

[30] Foreign Application Priority Data

Aug. 1, 1991 [IT] Italy .................. MI91A002147

[51] Int. Cl.⁵ .......................................... G01M 19/00
[52] U.S. Cl. .................................... 73/118.1; 324/456
[58] Field of Search ................ 73/118.1, 116, 119 R, 73/7; 324/452, 456

[56] References Cited

U.S. PATENT DOCUMENTS

| 3,576,425 | 4/1971 | Owen et al. | 73/159 |
| 4,235,091 | 11/1980 | Takano et al. | 73/118.1 X |
| 4,742,295 | 5/1988 | Nahman et al. | 324/133 |

FOREIGN PATENT DOCUMENTS

| 0490838 | 6/1992 | European Pat. Off. |
| 3308793 | 9/1984 | Fed. Rep. of Germany |
| 2149045 | 3/1973 | France |
| WO8302162 | 6/1983 | PCT Int'l Appl. |
| 541743 | 3/1977 | U.S.S.R. |

Primary Examiner—Jerry W. Myracle
Attorney, Agent, or Firm—Stevens, Davis, Miller & Mosher

[57] ABSTRACT

A driving belt (2) operatively mounted on at least a first (3a) and second (4) pulleys electrically insulated from each other, is provided with an electrically conductive covering fabric acting in contact relationship with the pulleys. By applying an electric voltage to the pulleys (3a, 4) the electric resistance value offered by the belt (2) is detected and this value is compared with a reference value to which a given degree of wear of the belt corresponds. When the detected resistance value is greater than the reference value, a danger signal is emitted. The danger signal is inhibited during the belt operation and during a predetermined waiting time starting from the moment of the belt stopping in order to avoid the resistance detection to be altered by electrostatic charges present on one of the pulleys (3a, 4) and/or the high temperature in the vicinity of the belt (2).

14 Claims, 2 Drawing Sheets

METHOD AND APPARATUS TO CHECK THE STATE OF WEAR IN A COVERING FABRIC OF A DRIVING BELT

BACKGROUND OF THE INVENTION

The present invention relates to a method and apparatus to check the state of wear in a coating fabric of a driving belt.

It is well known that for driving belts periodical inspections and/or replacements are required in order to avoid the risk, above all where positive drive belts are concerned, of the mechanical devices or members driving or driven by the belt being damaged, which would occur in case of accidental breakage of the belt itself.

Belts are usually comprised of an elastomeric body and a coating fabric applied to at least one of the belt surfaces designed to come into contact with the active surfaces of the belt pulleys.

In toothed belts this fabric is provided to coat the belt toothing designed to mesh with the pulley teeth.

In many cases the periodical inspection and/or replacements carried out directly by the person utilizing and/or taking care of the machine or apparatus on which the belt is mounted, is not sufficient to avoid the risk of breakage of the belt resulting from the wear of the coating fabric for example.

For the purpose of avoiding this problem, the applicant has developed a method and apparatus capable of checking the acceptability of the state of wear of the coating fabric in a driving belt in a completely automatic manner.

In particular this method and apparatus, being the object of the European Patent Application No. 91830544.2, disclose the use of a driving belt, a toothed belt for example, provided with a reinforcing textile cover applied to the work surface acting in contact with the pulleys.

The covering fabric is treated with electrically conductive charges so that, by applying an electric voltage between two pulleys engaging the belt which are electrically insulated from each other, it is possible to detect the resistance offered to the passage of current by at least two belt branches kept taut between said pulleys.

The belt use brings about the progressive consumption of the electrically conductive charges of the covering fabric and, consequently, the progressive increase in the detectable resistance value, so that, based on the detected resistance value, it is possible to ascertain to the state of wear of the belt fabric.

In particular, the resistance value detected on the belt is provided to be compared with a previously input resistance value corresponding to a given state of wear of the belt fabric.

When the belt fabric resistance overcomes the previously input value, a danger signal is emitted which informs the operator about the necessity of replacing the belt, which operation must be planned in due time in order to avoid the occurrence of irreparable damage not only to the belt but also to the motor to which the belt is connected.

SUMMARY OF THIS INVENTION

In accordance with the present invention it has been found that for the purpose of achieving an efficient and reliable danger signal, said signal need to be conveniently inhibited during the belt operation as well as over a predetermined period of time referred to as waiting time included between the moment at which the belt operation is interrupted and the moment at which the measurement of a parameter selected from the electric resistance of the fabric and the temperature of said fabric, takes a constant value; in this way the operation of the checking apparatus is not affected by anomalous conditions that have been deemed to consist for example in the presence of electrostatic charges on one or more of the pulleys and/or the presence of high temperatures on the belt and in the vicinity of the belt.

In particular, the invention relates to a method for checking the state of wear of the covering fabric in a driving belt applied to a motor, in which said driving belt, provided with a covering fabric treated with electrically conductive charges acting in contact relationship with at least first and second pulleys electrically insulated from each other and the setting in rotation of which brings about the operation of the belt itself, is submitted to the following steps:

applying a predetermined electric voltage between the first and second pulleys;

measuring an electric resistance value offered by at least two branches of said belt, kept taut between the first and second pulleys;

comparing the detected electric resistance value with a previously input electric resistance value corresponding to a given state of wear of the covering fabric of the belt;

signalling a state of danger when the detected electric resistance value overcomes said previously input value, characterized in that it further comprises the following steps:

a) stopping the belt operation before said step of applying electric voltage is activated;

b) waiting for the elapsing of a previously input time, starting from the moment at which the belt operation is stopped;

c) enabling the danger signalling on expiring of the preset waiting time, said signalling being kept disabled when the time elapsing between the belt motion stopping and the activation of the electric voltage applying step is lower that the value of said preset waiting time, as well as during the belt operation.

The danger signalling enabling step is preferably carried out through inhibition of said disabling step, at least over a predetermined delay time starting from the moment at which the predetermined electric voltage applying step is activated.

The waiting time is preset by chronometric detection of the time elapsing from the moment at which the belt operation is stopped to the moment at which the resistance offered by said belt branches takes a substantially constant value.

In a preferential solution of the invention, during said waiting step the following steps are further carried out:

detecting the temperature in the vicinity of the belt;

comparing the temperature value detected in the vicinity of the belt with a previously input reference temperature value;

enabling the danger signalling when the temperature value detected close to the belt is lower than the reference temperature value, said waiting time corresponding to the time elapsing between the belt operation stopping and the moment at which the detected temperature value is lower than the previously input reference value.

According to a further object of the invention an apparatus for checking the state of wear of a driving belt fabric is provided which comprises:

- a covering fabric treated with electrically conductive charges, applied to said belt and acting in contact relationship with at least a first and a second pulley electrically insulated from each other, the setting in rotation of which brings about the belt operation;
- an electric circuit having respective poles connected to the first and second pulleys respectively for applying a predetermined electric voltage to at least two branches of said belt extending between the first and second pulleys;
- detecting means associated with said electric circuit for detecting the electric resistance offered by said belt branches;
- comparing means to compare the electric resistance values detected by the detecting means with a previously input electric resistance value corresponding to a given state of wear of the belt;
- signalling means interlocked to said comparing means for signalling a state of danger when the detected electric resistance value overcomes the preset electric resistance value; characterized in that it further comprises:
- disabling means arranged to deactivate the signalling means during the driving belt operation and for a given waiting time starting from the moment at which the belt motion stopping occurs.

More particularly the signalling means is comprised of a diode having one pole connected to said comparing means and a second pole connected to an auxiliary electric circuit branch to be fed concurrently with the application of electric voltage to said pulleys and carrying said disabling means, said diode being arranged to emit the danger signalling when on one of the two poles, selectively predetermined, an electric signal of higher value than the electric signal existing on the other pole is present.

The comparing means preferably comprises at least one comparator-inverter having one input pole arranged to receive an input signal correlated with the resistance value detected on the belt branches, a second input pole arranged to receive a reference signal corresponding to the predetermined resistance value and an output pole arranged to send an output signal to the signalling means when the first input signal has a lower value than the first reference signal.

In turn, the disabling means comprises a second comparator-inverter acting on the auxiliary circuit branch and having one input pole arranged to receive an input signal, a second input pole arranged to receive a reference signal and an output pole connected to said diode for interrupting the enabling signal when the input signal overcomes the reference signal value, at least a primary timer designed to emit the input signal depending on the duration of the waiting time from the moment at which the electric power in the auxiliary circuit branch is cut off operating upstream of said first input pole.

Advantageously provision is also made for a delay timer acting upstream of said primary timer in order to delay for a predetermined time the feeding of the input signal to the first input pole of said second comparator-inverter.

Said disabling means may also be comprised of at least a thermostatic probe to be positioned on the driving belt fabric and connected to the auxiliary circuit branch in order to send an electric disabling signal to the second pole of the diode when the temperature of the belt overcomes a predetermined value.

In a preferential solution, one of said pulleys is arranged to operate a cooling pump in a motor-vehicle engine, said pump being electrically insulated from said engine.

BRIEF DESCRIPTION OF THE DRAWINGS

Further features and advantages of the invention will become more apparent from the detailed description of a preferred embodiment of a method and apparatus for checking the state of wear of a driving belt in accordance with the invention, given hereinafter by way of non-limiting example with reference to the accompanying drawings, in which.

DETAILED DESCRIPTION OF PREFERRED EMBODIMENTS

Figure 1:
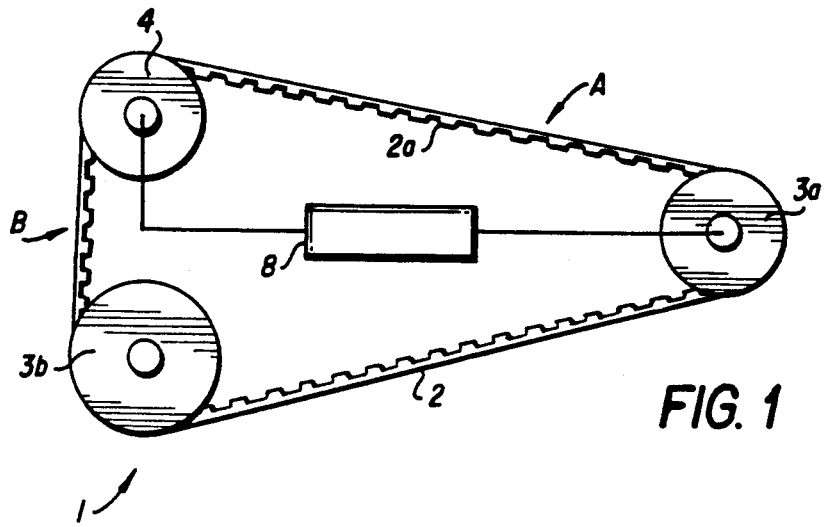
FIG. 1 is a diagrammatic side view of a driving belt operatively mounted on respective pulleys, on two of which an apparatus for carrying into effect the checking method in accordance with the present invention operates.

Referring to the drawings, an apparatus for checking the state of wear of a driving belt in accordance with the present invention has been generally identified by reference numeral 1.

Figure 3:
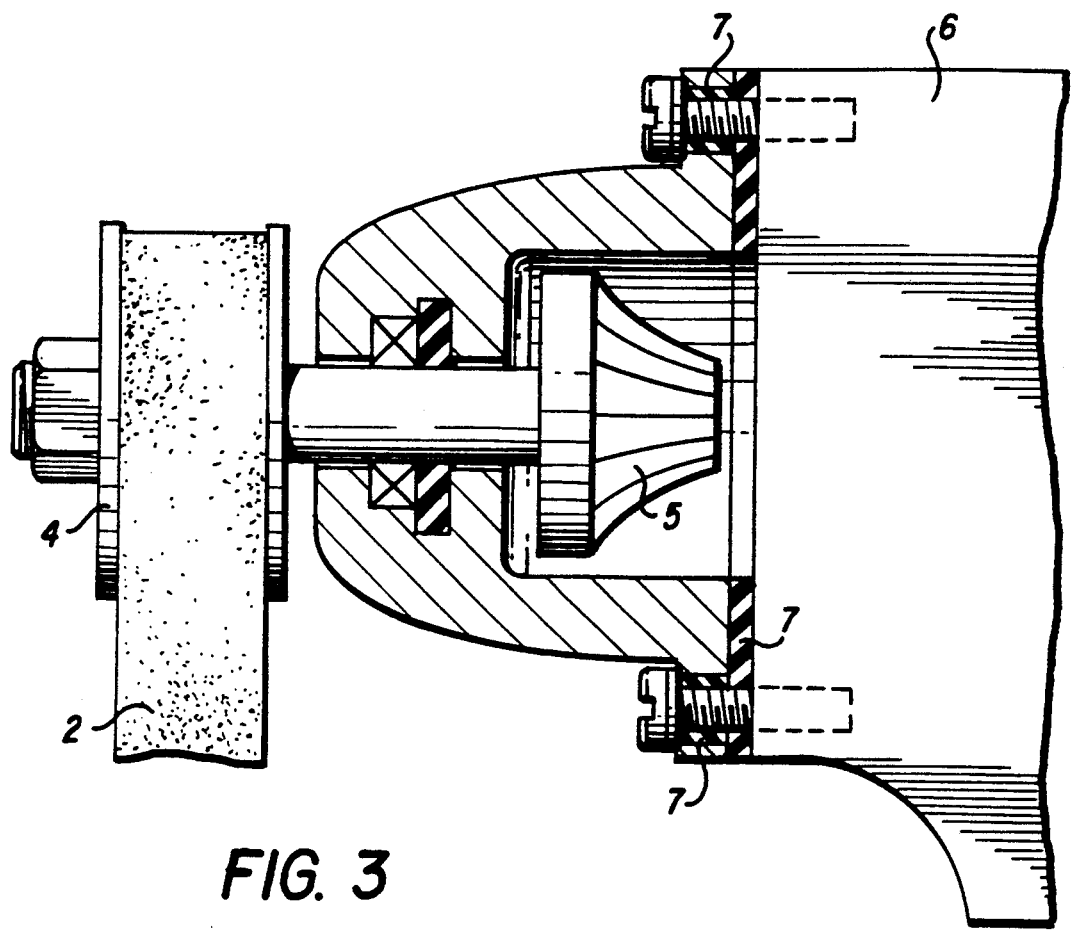
FIG. 3 is a diagrammatic part-sectional view of one of the pulleys arranged to operate a cooling pump electrically insulated from a motor-vehicle engine block.

Apparatus 1 provides for the use of a driving belt 2 operatively engaged to one or more first pulleys 3a, 3b and at least a second pulley 4 electrically insulated from the first pulleys 3. In the embodiment shown the belt 2 is installed on a motor-vehicle engine and the first pulleys 3a, 3b are respectively connected to the crankshaft and alternator belonging to said engine. The second pulley 4 is advantageously arranged to operate a cooling pump 5, usually provided in the engine and electrically insulated from the engine block 6 upon interposition of one or more gaskets (FIG. 3) 7.

The belt 2 which can be either of the trapezoidal, or "flat" or "poly-V" type, or, as in the embodiment shown, a toothed belt, is provided, on a work surface 2a thereof, with at least a textile covering fabric treated with electrically conductive charges, acting in contact relationship with the pulleys 3a, 3b and 4. This fabric is not shown in the accompanying drawings and will not be further described as it is disclosed in European Patent Application No. 91830544.2, in the name of the present assignee. To the ends of the present invention it is sufficient to note that the presence of the fabric treated with electrically conductive charges gives the belt 2 a predetermined electric resistance that will tend to progressively increase as the belt is used in time, due to the progressive consumption of the covering fabric.

Figure 2:
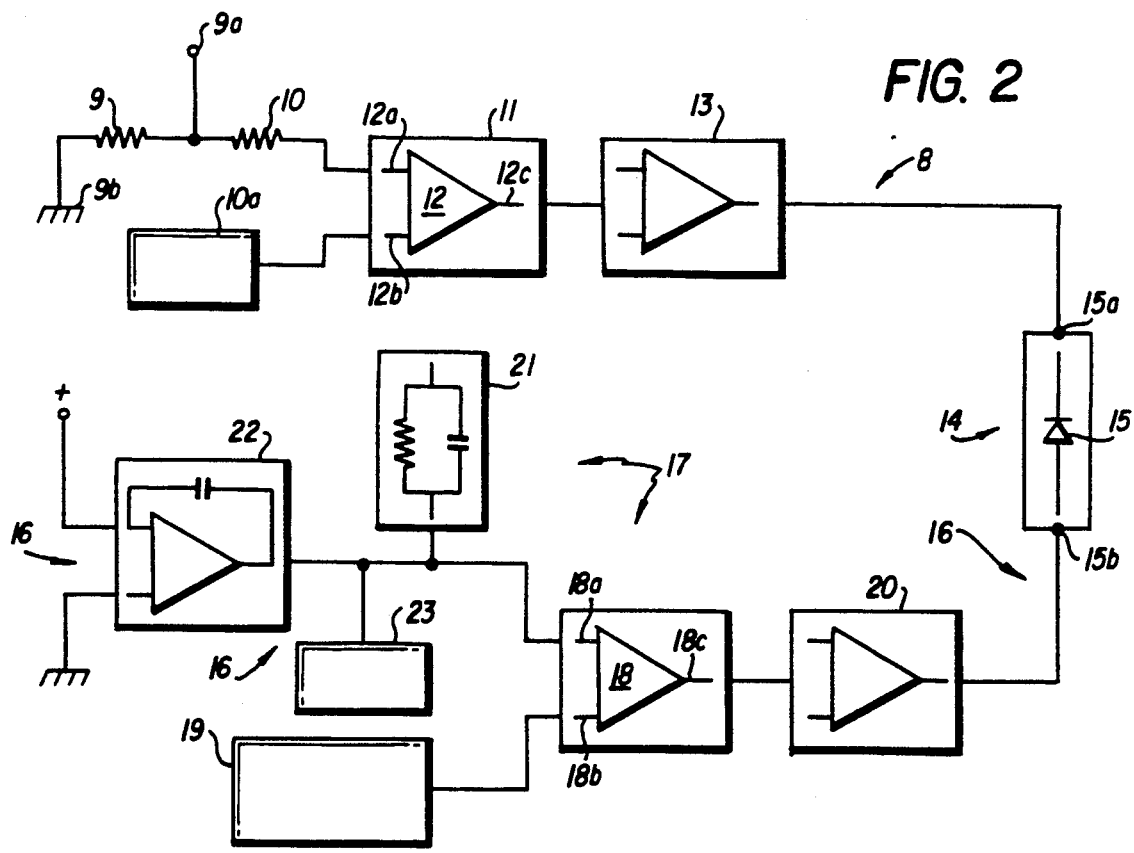
FIG. 2 is a schematic diagram of the checking apparatus of the invention.

In accordance with apparatus 1 the belt 2 is further associated with an electronic control unit generally identified by 8 in FIG. 1 which is comprised, as better shown in FIG. 2, of an electric circuit 9 the respective poles 9a, 9b of which are connected to one of the first pulleys 3a and the second pulley 4 in order to apply a predetermined electric voltage to at least two belt branches, denoted by A and B in FIG. 1 and included between the pulleys.

For example a positive polarity is applied to pulley 4 through a power supply reaching the rotating portion of the pulley through the metal bearings. Pulley 3a is grounded.

The two belt branches A, B as regards the current passage behave like two resistances connected in parallel, the effects of which give rise to an overall resistance denoted Rx in FIG. 2 from the value of which it is possible to ascertain to the belt state of wear.

Connected to the electric circuit 9 is detecting means 10 designed to detect the resistance Rx value offered by the belt 2, combined with comparing means 11 designed to compare the resistance Rx value with a preset resistance value corresponding to a predetermined wear degree of the belt 2.

In particular, the comparing means 11 preferably consists of a comparator-inverter 12, of the FET (field-effect transistor) type, having one input pole 12a connected to the detecting means 10 which is essentially comprised of a connecting circuit branch passed through by a current flux proportional to the resistance Rx value offered by the belt 2.

The comparator-inverter 12 also has a second input pole 12b, to which an electric signal of a predetermined value is input through one additional feed unit 10a, which predetermined value corresponds to the preset resistance value, as well as an output pole 12c arranged to emit an electric output signal when the input signal coming from the connecting branch 10 is lower than the reference signal input to the second input pole 12b.

The output signal coming from the comparator-inverter 12, previously amplified by an amplifying signal 13, is sent to signalling means 14 preferably comprising at least a light emitting diode 15 having one pole 15a connected to the first comparator-inverter 12 and a second pole 15b terminating at an auxiliary electric circuit branch 16 to be fed concurrently with the application of electric voltage to pulleys 3a and 4. The diode 15 enables the passage of current only when a situation occurs in which in one of its poles and more particularly the second pole 15b, an electric signal is present, concurrently with the absence of the electric signal on the other pole 15a.

In accordance with the present invention, disabling means 17 acts on the auxiliary circuit branch 16 which, as better clarified in the following, is arranged to deactivate the signalling means 15 while the driving belt 2 is in operation and also for a preset waiting time, preferably included between two and six minutes, starting from the moment at which the belt operation is stopped.

The waiting time can vary depending upon the belt type and features and the features of the engine to which the belt is applied.

In greater detail, the disabling means 17 is preferably comprised of a second comparator-inverter 18, quite similar to the first comparator-inverter 12, having one input pole 18a arranged to receive an electric input signal following from the auxiliary circuit branch 16 feeding, as well as a second input pole 18b designed to receive a reference signal coming from a second additional feed unit 19.

The second comparator-inverter 18 finally has an output pole 18c designed to emit an electric enabling signal only when the signal coming from the first input pole 18a has a lower value than the reference signal sent to the second input pole 18b. The enabling signal will reach the second pole 15b of the diode 15 upon passing through a second signal amplifier 20.

In other words, the second comparator-inverter 18 acts in such a manner that the enabling signal is interrupted when the input signal reaching the first input pole 18a exceeds the value of the reference signal input to the second input pole 18b.

Combined with the second comparator-inverter 18 is at least a primary timer 21 consisting for example of a mere "RC" circuit connected to the first input pole 18a and designed to emit the input signal according to the duration of the desired waiting time, for example approximately three minutes from the moment at which the application of electric voltage to the pulleys 3a, 4 is interrupted, being consequently also interrupted the power supply to the auxiliary circuit branch 16.

In addition, at least a delay timer 22 is provided upstream of the primary timer 21 and it is designed to cause the feeding of the input signal to the first input pole 18a of the second comparator-inverter 18, at least for a predetermined delay time preferably corresponding to 0.2 seconds and at all events included between 0.1 and 0.4 seconds for example.

According to one embodiment it is also possible to provide for the presence of monostable oscillators disposed respectively between the circuit elements referenced at 11, 13 and 18, 20 in FIG. 2 and the function of which is to prolong the switching on of the LED 15.

Still in accordance with the present invention, provision may be also made for the use of a thermic probe in combination with, or optionally in place of the primary and delay timers 21 and 22. Said thermal probe will be positioned on the belt 2 fabric and operatively connected to the first input pole 18a of the second comparator-inverter 18 in order to infeed the input signal when the temperature close to the belt overcomes a predetermined limit value.

This thermal probe, referenced at 23 in FIG. 2, can consist of a NTC (Negative Temperature Coefficient)-type device for example, and not further described as known per se.

In accordance with the checking method being the object of the present invention as well, operation of apparatus 1 described above mainly as regards structure, is as follows.

Should the belt 2 exhibit an acceptable state of wear, the voltage drop produced by the passage of current through the resistance Rx, that is the belt itself, causes an input signal of low value to reach the first input pole 12a of the first comparator-inverter 12, which low value is lower than the reference signal value sent to the second input pole 12b. Under this situation, the comparator-inverter 12 operating according to the Boolean logic sends an electric signal of high value to the first pole 15a of diode 15.

Under this situation the diode 15 will not be able to emit any signalling independently of whether there is an electric signal at the second pole 15b or not.

When on the contrary the resistance Rx offered by belt 2 is high, the input signal reaching the first input pole 12a of the first comparator-inverter 12 is higher than the reference signal sent to the second pole 12b. Under this situation, the outcoming signal from the first comparator-inverter 12 will have a low or zero value. Therefore the diode 15 will be in a position to carry into effect the danger signalling depending upon the state of signal at the second pole 15 of the diode itself.

Simultaneously with the application of electric voltage to pulleys 3a and 4, the power supply to the auxiliary circuit 16 occurs. The signal input to said circuit, after passing through the delay timer 22 reaches the first pole 18a of the second comparator-inverter 18 that, in this case too due to the principle of the Boolean logic, will send a low value signal to the second pole 15b of the diode 15, in that the signal on the first input pole 18a is higher than the reference signal present on the second input pole 18b. Under this situation, the enabling signal to the signalling means 14 is interrupted and this condition will remain unchanged unitl the interruption of the electric supply to the circuit 9 and auxiliary circuit branch 16 is carried out at least for the preset waiting time. Under this situation the primary timer 21 is also loaded, which will cause the storage of the waiting time thereinto.

If the signal change of state at the first pole 15a of diode 15 occurs while the belt is in operation, that is the engine is running and therefore a power supply is present in the electric circuit 9 and the auxiliary circuit branch 16, the absence of electric signal on the second pole 15b of diode 15 prevents the latter from emitting the danger signalling even if a signal decay at the first pole 15a has occured.

Advantageously, in this way the risk that diode 15 may erroneously give a danger indication is eliminated, in that the electric signal drop at the output of the first comparator-inverter 12 could be caused by a frictitious increase of resistance Rx, due to the accumulation of electrostatic charges on the electrically insulated second pulley 4 for example, as a result of the belt movement.

The belt inspection is carried out by interrupting the operation of said belt together with the power supply to the electric circuit 9 and auxiliary circuit branch 16 and waiting for the end of the preset waiting time, in order to subsequently apply voltage again to the circuit 9 and auxiliary branch 16.

Should the voltage application take place before the end of the waiting time, the diode 15 will not be able to emit any danger signalling in that the primary timer 21, and the thermal probe 23 if present, will go on feeding the first input pole 18a of the second comparator-inverter 18 keeping the activation signal of the second pole 15b of the diode itself interrupted.

It is therefore possible to eliminate the risk that diode 15 may erroneously emit a danger signalling when the fictitious value of resistance Rx, in spite of the operation being stopped, can be affected by the presence of electrostatic residual charges on the second pulley 4, as well as by the high temperature present in the vicinity of the belt 2.

In fact it has been found that the belt immediately after being stopped exhibits high resistance values, in the order of 1.6 to 2 MΩ, and it is therefore necessary to wait for a certain lapse of time before the insulated pulley 4 may completely discharge to earth and the temperature in the vicinity of the belt 2 may reach a sufficiently low value. This waiting time can be input by chronometric measurement of the time elaspsing from the stopping of the belt operation to the moment at which the resistance Rx offered by the belt itself reaches a substantially constant value.

Figure 4:
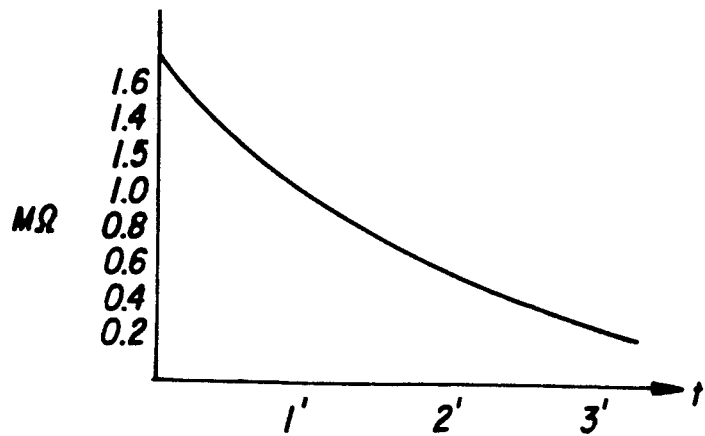
FIG. 4 is a graph showing, by way of example, the variation in time of the detectable resistance of a belt being tested, starting from the moment at which the belt operation is stopped.

The decay of the resistance Rx value in time is shown by way of example in the graph of FIG. 4 reproducing the resistance Rx value on the ordinates and the time elapsing from the stopping of the belt 2 operation on the abscissas.

When the application of electric voltage to the circuit 9 and auxiliary branch 16 occurs after a longer time than the waiting time, the second comparator-inverter 18 within the time permitted by the delay timer 22 emits the enabling signal from the output pole 18c in that the reference signal from the second input pole 18b will be higher than the signal present on the first input pole 18a. The diode 15 therefore will be in a position to be switched on so as to emit the danger signalling if, in the presence of a high resistance value offered by the belt, there is no signal on the first pole 15a of the diode itself.

The waiting time will be computed for each belt after establishing the motor to which the belt is applied for motion transmission.

In order to establish the waiting time, the belt is kept in rotation being subjected to torque and rated revolutions over a predetermined period of time that could be included between 0 and 1000 hours for example.

The predetermined time takes lower or higher values depending on whether it refers to a new belt or a belt that has been used for a long time respectively. When the belt is new the resistance values are low and therefore can be less affected by temperature than those relating to a belt that has been running for a long time.

Subsequently the belt is stopped and the calculation of the curve joining together, depending upon time, a first electric resistance value of the fabric or temperature value of the fabric corresponding to the moment at which the belt has stopped and a second constant-development value of one of the two cited parameters, is carried out.

This time elapsing between the above two values is the preset time referred to beforehand.

As can be seen in FIG. 4, the preset time is about 3'. The graph in FIG. 4 refers to a toothed belt having the following features:
pitch = 9.525 mm
tooth depth = 3.30 mm
tooth root (between the two intersection points of the tangents to the flanks with the line connecting the bottom of all recesses) = 5.75 mm
flank profile = a parabolic curve
longitudinal resistant insert piece = No. 14 fiberglass cords of the type commonly used in driving belts
longitudinal extension = 923.925 mm
teeth covering fabric:
nylon 66
chemical composition according to Italian application 22 335 A/90.

In greater detail, two electrically conductive polychloroprene polymer-based layers containing conductive charges are applied to the reinforcing fabric.

As it has been indicated in the European Patent application 91830544.2 as an alternative solution to the polychloroprene-base polymer, all other base polymers adapted for driving belts can be used, for example hydrogenated cyanocarbon-based polymers (HNBR) or special chlorosulfonates (ACSM).

The conductive charges preferably consist of a conductive black known as "carbon black" and the charges can have sizes of 200 A (Angstrom).

The layer disposed towards the belt body is formed with a compound mainly containing carbon blank (50 parts by 100 parts of polymer).

The external layer corresponding to the work surface is in turn formed with a compound mainly containing self-lubricating graphite (60 parts by 100 parts of polymer).

The engine to which the belt is applied is defined by the following data:

Power=60 HP

The engine is a four-cylinders with camshaft on top, piston displacement 1.4 liters and 5,500 peak r.p.m.

The waiting time of 3 minutes has been computed by rotating the belt for 300 hours at a torque of 2.5 kg and 6000 r.p.m.

The invention solves the problem of informing the user in due time of the necessity of replacing the belt before an irreparable damage to the transmission and the members associated therewith occurs.

As seen, the danger signalling emitted by the method and apparatus in question cannot be subject to errors resulting for example from the accumulation of electrostatic charges on the insulated pulley 4, capable of increasing the fictitious belt resistance.

In addition, by virtue of the waiting time being preset, as well as the possible use of the thermal probe, an appropriate thermal stabilization of the belt 2 before carrying out the inspection is enabled.

In fact a high temperature in the belt could alter the detectable resistance value and release an alarm that actually could be nonexistent.

Not only the device in question is very reliable, but in addition its structure is very simple, has a reduced production cost and can be readily applied to any motor or kinematic mechanism using driving belts.

Obviously, many modifications and variations may be made to the invention as conceived, all of them falling within the scope of the inventive idea.

We claim:

1. A method for checking the state of wear of covering fabric in a driving belt, in which said driving belt, provided with a covering fabric treated with electrically conductive charges acting in contact relationship with at least a first pulley and a second pulley which are electrically insulated from each other and the setting in rotation of which brings about the operation of the belt, said method comprising the following steps:
   applying a predetermined electric voltage between the first and second pulleys;
   measuring ma electric resistance value offered by at least two branches (A, B) of said belt, kept taut between the first and second pulleys;
   comparing the detected electric resistance value (Rx) with a previously input electric resistance value corresponding to a given state of wear of the covering fabric of the belt;
   signalling a state of danger when the detected electric resistance value (Rx) overcomes said previously input value, characterized in that it further comprises the following steps:
   a) stopping the belt operation before said step of applying electric voltage is activated;
   b) waiting for the elapsing of a previously input time, starting from the moment at which the belt operation is stopped;
   c) enabling the danger signalling upon expiration of the preset waiting time, said signalling being kept disabled when the time elapsing between the belt motion stopping and the activation of the electric voltage applying step is lower that the value of said preset waiting time, as well as during the belt operation.

2. A method according to claim 1, in which said danger signalling enabling step is preferably carried out through inhibition of said disabling step, at least over a predetermined delay time starting from the moment at which the predetermined electric voltage applying step is activated.

3. A method according to claim 2, in which said delay time has a value included between 0.1 and 0.4 seconds.

4. A method according to claim 1, in which said waiting time is preset by chronometric detection of the time elapsing from the moment at which the belt operation is stopped to the moment at which the resistance offered by said belt branches (A, B) takes a substantially constant value.

5. A method according to claim 1, in which said waiting time has a value included between two and six minutes.

6. A method according to claim 1, in which during said waiting step the following steps are further carried out:
   detecting the temperature in the vicinity of the belt;
   comparing the temperature value detected in the vicinity of the belt with a previously input reference temperature value;
   enabling the danger signalling when the temperature value detected close to the belt is lower than the reference temperature value, said waiting time corresponding to the time elapsing between the belt operation stopping and the moment at which the detected temperature value is lower than the previously input reference value.

7. A method for checking the state of wear of a driving belt, in which said driving belt, provided with a covering fabric treated with electrically conductive charges acting in contact relationship with at least a first pulley and a second pulley which are electrically insulated from each other and the setting in rotation of which brings about the operation of the belt, said method comprising the following steps:
   applying a predetermined electric voltage between the first and second pulleys;
   measuring ma electric resistance value of at least two branches (A, B) of said belt, kept taut between the first and second pulleys;
   comparing the first electric resistance value with a previously input electric resistance value corresponding to a given state of wear of the belt;
   signalling a state of danger when the first electric resistance value is greater than said previously input value, said method further comprising the following steps:
   stopping the belt operation before said step of applying electric voltage is activated;
   detecting the temperature in the vicinity of the belt;
   comparing the temperature value detected in the vicinity of the belt with a previously input reference temperature value;
   enabling the danger signalling when the temperature value detected close to the belt is lower than the reference temperature value, said signalling being kept disabled when the temperature value detected close to the belt is higher than the reference temperature value, as well as during the belt operation.

8. An apparatus for checking the state of wear of a driving belt comprising:

a covering fabric treated with electrically conductive charges, applied to said belt and acting in contact relationship with at least a first and a second pulley electrically insulated from each other, the setting in rotation of which brings about the belt operation;

an electric circuit having respective poles connected to the first and second pulleys respectively for applying a predetermined electric voltage to at least two branches (A, B) of said belt extending between the first and second pulleys;

detecting means associated with said electric circuit for detecting the electric resistance (Rx) of said belt branches (A, B);

comparing means to compare the electric resistance (Rx) values detected by the detecting means with a previously input electric resistance value corresponding to a given state of wear of the belt;

signalling means connected to said comparing means for signalling a state of danger when the detected electric resistance (Rx) value overcomes the preset electric resistance value; said apparatus further comprising:

disabling means connected to deactivate the signalling means during belt operation and for a given waiting time starting from the moment at which the belt stops operation.

9. An apparatus according to claim 8, in which said signalling means is comprised of a diode having one pole connected to said comparing means and a second pole connected to an auxiliary electric circuit branch to be fed concurrently with the application of electric voltage to said pulleys and carrying said disabling means, said diode being arranged to emit the danger signalling when on one of the two poles, selectively predetermined, an electric signal of higher value than the electric signal existing on the other pole is present.

10. An apparatus according to claim 9, in which said comparing means preferably comprises at least a first comparator-inverter having one input pole arranged to receive an input; signal correlated with the resistance value (Rx) detected on the belt branches (A, B), a second input pole arranged to receive a reference signal corresponding to the predetermined resistance value and an output pole arranged to send an output signal to the signalling means when the first input signal has a lower value than the first reference signal.

11. An apparatus according to claim 10, in which said disabling means comprises a second comparator-inverter acting on the auxiliary circuit branch and having one input pole for receiving an input signal, a second input pole for receiving a reference signal and an output pole connected to said diode for interrupting the enabling signal when the input signal is greater than the reference signal value, at least a primary timer designed to emit the input signal depending on the duration of the waiting time from the moment at which the electric power in the auxiliary circuit branch is cut off operating upstream of said first input pole.

12. An apparatus according to claim 11, further comprising a delay timer acting upstream of said primary timer in order to delay for a predetermined time the feeding of the input signal to the first input pole of said second comparator-inverter.

13. An apparatus according to claim 9, in which said disabling means is comprised of at least a thermic probe to be positioned in the vicinity of the driving belt and connected to the auxiliary circuit branch in order to send an electric disabling signal when the temperature close to the belt is higher than a predetermined value.

14. An apparatus according to claim 8, in which one of said pulleys operates a cooling pump of a motor-vehicle engine, said pump being electrically insulated from said engine.

* * * * *